US009080490B2

(12) United States Patent
Itou

(10) Patent No.: US 9,080,490 B2
(45) Date of Patent: Jul. 14, 2015

(54) SELECTIVE CATALYTIC REDUCTION SENSOR

(75) Inventor: Tomoyuki Itou, Fujisawa (JP)

(73) Assignee: ISUZU MOTORS LIMITED, Tokyo (JP)

( * ) Notice: Subject to any disclaimer, the term of this patent is extended or adjusted under 35 U.S.C. 154(b) by 286 days.

(21) Appl. No.: 13/697,929

(22) PCT Filed: May 16, 2011

(86) PCT No.: PCT/JP2011/061209
§ 371 (c)(1),
(2), (4) Date: Nov. 14, 2012

(87) PCT Pub. No.: WO2011/145571
PCT Pub. Date: Nov. 24, 2011

(65) Prior Publication Data
US 2013/0061665 A1 Mar. 14, 2013

(30) Foreign Application Priority Data
May 17, 2010 (JP) .................................. 2010-113761

(51) Int. Cl.
*G01N 7/00* (2006.01)
*F01N 3/20* (2006.01)
*F01N 3/10* (2006.01)
*F01N 13/00* (2010.01)
*G01N 1/22* (2006.01)
*F01N 3/021* (2006.01)

(52) U.S. Cl.
CPC ................ *F01N 3/208* (2013.01); *F01N 3/103* (2013.01); *F01N 13/009* (2014.06); *F01N 3/021* (2013.01); *F01N 2560/06* (2013.01); *F01N 2610/02* (2013.01); *F01N 2610/1406* (2013.01); *F01N 2610/1453* (2013.01); *F01N 2900/0404* (2013.01); *F01N 2900/1814* (2013.01); *F01N 2900/1818* (2013.01); *G01N 1/2294* (2013.01); *Y02T 10/24* (2013.01)

(58) Field of Classification Search
CPC ...................................................... G01N 1/2294
USPC ......................................... 73/19.01, 305, 309
See application file for complete search history.

(56) References Cited

U.S. PATENT DOCUMENTS
2007/0202019 A1  8/2007  Nishina et al.

FOREIGN PATENT DOCUMENTS
JP   2000-303826   10/2000
JP   3686668       8/2005
JP   2009-299526   12/2009

OTHER PUBLICATIONS

International Search Report of Corresponding PCT Application PCT/JP2011/061209 mailed Aug. 16, 2011.
(Continued)

*Primary Examiner* — Herzon E Williams
*Assistant Examiner* — Rodney T Frank
(74) *Attorney, Agent, or Firm* — Staas & Halsey LLP

(57) ABSTRACT

A Selective Catalytic Reduction sensor that does not degrade a measurement accuracy of a quality sensor even when a remaining amount of a urea tank is reduced. A quality sensor is installed between a minimum remaining amount liquid level and a bottom portion of the urea tank; a drop pipe is installed from a ceiling portion of the urea tank to a top space in the urea tank; a support is installed from a bottom portion to the ceiling portion of the urea tank; the quality sensor and the drop pipe are integrated through the support; and a bubble diffusion region caused by the urea aqueous solution dropping from the drop pipe is out of a sensitive region of the quality sensor.

5 Claims, 6 Drawing Sheets

(56) References Cited

OTHER PUBLICATIONS

Patent Abstracts of Japan, Publication No. 2000-303826, Published Oct. 31, 2000.

Patent Abstracts of Japan, Publication No. 2009-299526, Published Dec. 24, 2009.

Written Opinion of the International Searching Authority mailed Aug. 16, 2011 in corresponding International Application No. PCT/JP2011/061209.

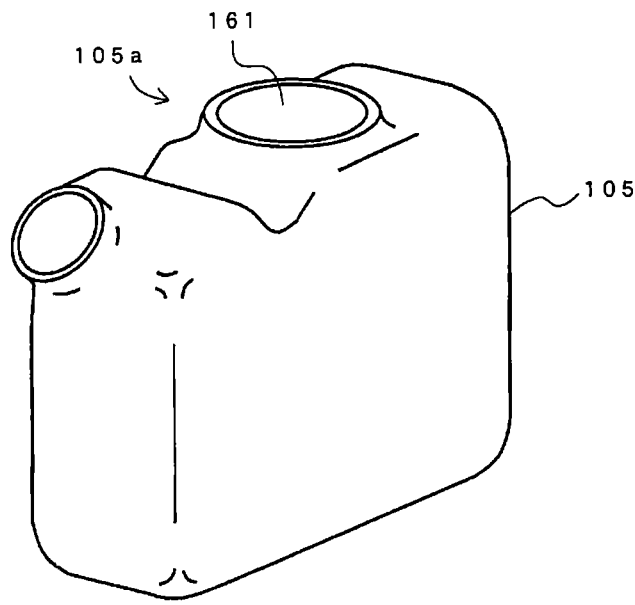
F I G. 6
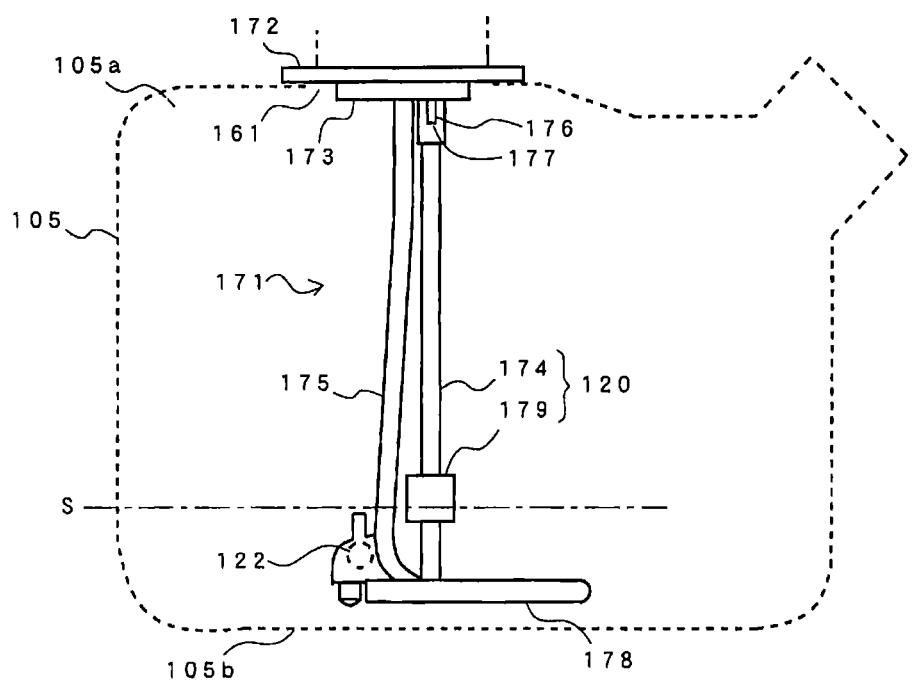
F I G. 7

SELECTIVE CATALYTIC REDUCTION SENSOR

CROSS-REFERENCE TO RELATED APPLICATIONS

This application claims the benefit of Japanese Patent Application No. 2010-113761, filed on May 17, 2010, the contents of which is incorporated herein by reference, which serves as priority for PCT Application No. PCT/JP2011/061209, filed May 16, 2011.

TECHNICAL FIELD

The present invention relates to an Selective Catalytic Reduction ("SCR") sensor attached to a urea tank storing urea aqueous solution for purifying exhaust gas of an engine, and relates to an SCR sensor of which the measurement accuracy of a quality sensor is not degraded even when a remaining amount of a urea tank is reduced.

BACKGROUND ART

As an exhaust gas purification system for purifying NOx in exhaust gas of a diesel engine, an SCR system using an SCR device has been developed.

The SCR system supplies urea aqueous solution to an exhaust gas upstream of the SCR device, generates ammonia by the heat of the exhaust gas, and reduces and purifies NOx on an SCR catalyst by the ammonia (see, for example, Patent Document 1).

PRIOR ART DOCUMENTS

Patent Document 1: Japanese Patent Application Publication No. 2000-303826

In order to drive while continuing to purify exhaust gas, a vehicle needs to store a sufficient amount of urea aqueous solution. Therefore, the vehicle is mounted with a urea tank, and a level sensor for detecting a remaining amount of urea aqueous solution is installed in the urea tank so that a lack of urea aqueous solution can be determined. Also, since a quality of the urea aqueous solution needs to be managed in order to stably maintain a good purification performance, a quality sensor for measuring a quality of the urea aqueous solution is installed in the urea tank. Also provided is an interconnection for transmitting a signal of the quality sensor outside the urea tank.

The vehicle is mounted with a supply module ("SM") for supplying the urea aqueous solution inside the urea tank to a destination. The supply module circulates the urea aqueous solution by increased pressure and recovers the circulated urea aqueous solution into the urea tank so that a necessary amount of urea aqueous solution can be injected into an exhaust pipe when necessary. Therefore, a dispensing pipe for dispensing the urea aqueous solution and a drop pipe for returning the recovered urea aqueous solution into the urea tank are installed in the urea tank.

As above, a plurality of sensors or a plurality of interconnections/pipes are installed in the urea tank. In order to simplify the task of assembling these members in the urea tank, it is desirable to make all the sensors or interconnections/pipes assembled into one body so that it becomes unnecessary to form a pedestal for each sensor or a hole for each pipe or install interconnections at the side of the urea tank. Such an assembly of a plurality of sensors or a plurality of pipes installed in the urea tank is called an SCR sensor.

However, the shapes or desirable installation positions of the sensors or pipes constituting the SCR sensor are different according to their respective requirements. In order to be able to detect a remaining urea aqueous solution amount between a full tank to an empty tank, the level sensor is configured such that a support guiding a float for liquid level detection is installed from a bottom to a ceiling portion of the urea tank. In order to be able to measure a reduced remaining urea aqueous solution amount, the quality sensor is installed between the bottom of the urea tank and a minimum remaining amount liquid level. In order to be able to dispense the remaining urea aqueous solution amount from the full tank to the empty tank, the dispensing pipe is installed from the bottom to the ceiling portion of the urea tank. For material saving, it is desirable that the drop pipe be formed short. The drop pipe is installed from the ceiling portion to an upper space of the urea tank, and is configured to drop the recovered urea aqueous solution into the urea tank.

In order to further simplify the task of attaching the SCR sensor, which is an assembly of a plurality of members that are different in shapes or desirable installation positions, in the urea tank, it is desirable that all the members are arranged intensively at a central portion of a tope side of the urea tank.

Therefore, as the SCR sensor and the urea tank, those of FIGS. 6 and 7 can be considered.

As shown in FIG. 6, an attachment hole 161, into which the SCR sensor is inserted and attached, is formed at a ceiling portion 105a of a urea tank 105.

As shown in FIG. 7, an SCR sensor 171 is provided with a ceiling panel 172 covering the attachment hole 161 of the urea tank 105. A top pedestal 173 facing inside the urea tank 105 is formed at a bottom surface of the ceiling panel 172. A support 174 of a level sensor 120 is attached to the top pedestal 173, and a dispensing pipe 175 and a drop pipe 176 are inserted into the top pedestal 173. The drop pipe 176 is short and protrudes immediately under the top pedestal 173, and a drop opening 177 is located at a top portion in the urea tank 105. The support 174 and the dispensing pipe 175 are longer and extend to near a bottom portion 105b of the urea tank 105. A flat stabilization plate 178 for fixing the support 174 and the dispensing pipe 175 to each other and stabilizing the SCR sensor 171 against buoyancy is provided at bottom ends of the support 174 and the dispensing pipe 175. The stabilization plate 178 is a pedestal for holding a suction opening (not shown) of the dispensing pipe 175, and is also an attachment pedestal for a quality sensor 122.

The quality sensor 122 is attached to one end portion of one side of the stabilization plate 178, with a sensitive surface 122a (see FIG. 8) facing outside the stabilization plate 178. Depending on the sensitivity or directionality of the quality sensor 122, a sensitive region F (see FIG. 8) of the quality sensor 122 for measuring a urea aqueous solution quality extends substantially around the sensitive surface 122a.

A float 179 of the level sensor 120 is allowed to move only in an axial direction with respect to the support 174. Inside the support 174, a plurality of proximity sensors (not shown) for detecting the proximity of the float 179 are arranged in parallel to the axial direction. The support 174 forms a frame member of the SCR sensor 171, and the quality sensor 122 in the bottom portion of the urea tank 105 and the drop pipe 176 in the top portion of the urea tank 105 are integrated through the support 174. In addition, although not shown, a temperature sensor is also attached to the SCR sensor 171. Also, although not shown, an interconnection of the quality sensor 122 or the temperature sensor is fixed to the dispensing pipe 175 by a binder or the like.

FIG. 8 is a side view of the SCR sensor 171 (an opposite side with respect to FIG. 7). The sensitive surface 122a of the quality sensor 122 faces toward a front of a paper plane, and the drop pipe 176 is located behind the dispensing pipe 175. FIG. 9 is a rear view of the SCR sensor 171. FIG. 10 is a top view of the SCR sensor 171 taken at a minimum remaining amount liquid level S. A virtual drop opening 176a is shown by projecting the drop opening 177 of the drop pipe 176. That is, when a remaining amount of urea aqueous solution inside the urea tank 105 is in the vicinity of the minimum remaining amount liquid level S, the urea aqueous solution from the drop pipe 176 is dropped into the virtual drop opening 176a.

By this configuration, all the members of the SCR sensor 171 are arranged at respective vertical positions to fulfill respective functions, and its extension in a horizontal direction is minimized, so that easy handling thereof is achieved. Also, the SCR sensor 171 can be attached to the urea tank 105 with a minimum work effort of nearly one touch just by inserting the SCR sensor 171 into the attachment hole 161 of the urea tank 105.

However, since all the members are arranged intensively at the central portion of the top of the urea tank 105 as described above, the quality sensor 122 and the drop pipe 176 are somewhat vertically aligned with each other. Therefore, when the urea aqueous solution is reduced to near the minimum remaining amount liquid level S, bubbles caused by the urea aqueous solution dropped from the drop pipe 176 are diffused into the sensitive region F of the quality sensor 122. When bubbles are present in the sensitive region F of the quality sensor 122, the quality sensor 122 cannot normally function, thus degrading the measurement accuracy. FIG. 8 shows a bubble diffusion region B where the bubbles are diffused. It can be seen that the bubble diffusion region B overlaps the sensitive region F.

SUMMARY OF THE INVENTION

It is an object of the present invention to solve the above problems and provide an SCR sensor that does not degrade the measurement accuracy of the quality sensor even when the remaining amount of the urea tank is reduced.

To achieve the object described above, an SCR sensor according to the present invention is an SCR sensor wherein a quality sensor for measuring a liquid quality between a minimum remaining amount liquid level and a bottom portion of a liquid tank and a drop pipe having a drop opening at a top space of the liquid tank are integrated through a support which is part of an assembly inserted into the liquid tank, and a bubble diffusion region caused by liquid dropping from the drop pipe is out of a sensitive region of the quality sensor.

A dispensing pipe for dispensing liquid from the liquid tank may be installed along the support; the quality sensor may be disposed at one side of the dispensing pipe; and the drop opening of the drop pipe may be disposed at an opposite side with respect to the quality sensor of the dispensing pipe.

Further, an SCR sensor according to the present invention is an SCR sensor attached to a urea tank storing urea aqueous solution for purifying exhaust gas of an engine, wherein a quality sensor for measuring a quality of the urea aqueous solution inside the urea tank is installed between a minimum remaining amount liquid level and a bottom portion of the urea tank, a drop pipe for dropping the urea aqueous solution, which is dispensed from the urea tank and temporarily stored outside the urea tank and then recovered, into the urea tank is installed from a ceiling portion to a top space of the urea tank, a support guiding a float for liquid level detection is installed from the bottom portion to the ceiling portion of the urea tank, the quality sensor and the drop pipe are integrated through the support, and a bubble diffusion region caused by the urea aqueous solution dropping from the drop pipe is out of a sensitive region of the quality sensor.

A dispensing pipe for dispensing urea aqueous solution from the urea tank may be installed along the support; the quality sensor may be disposed at one side of the dispensing pipe; and a drop opening of the drop pipe may be disposed at an opposite side with respect to the quality sensor of the dispensing pipe.

An assembly may be formed by integrating the quality sensor and the drop pipe through the support, and the assembly may be attached to the urea tank by being inserted into an attachment hole formed at the ceiling portion of the urea tank.

The present invention exhibits excellent effects such as the following.

The measurement accuracy of the quality sensor is not degraded even when the remaining amount of the urea tank is reduced.

BRIEF DESCRIPTION OF THE DRAWINGS

FIG. 6 is a skewed perspective view of a urea tank to which an SCR sensor is attached.

FIG. 7 is an opposite side view of an SCR sensor.

DETAILED DESCRIPTION

Hereinafter, preferred embodiments of the present invention will be described with reference to the accompanying drawings.

Figure 1:
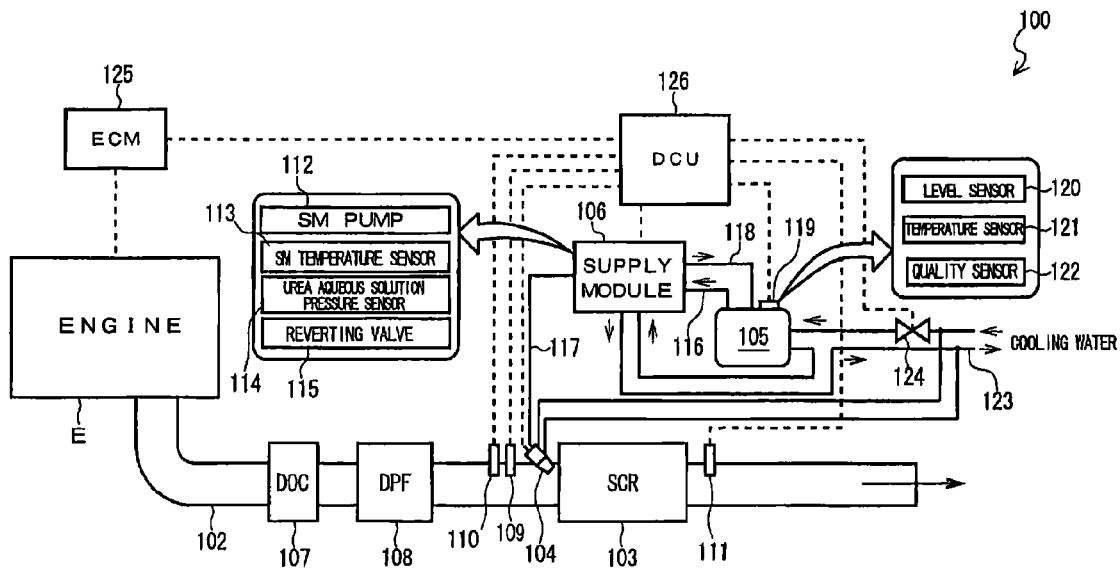
FIG. 1 is a configuration diagram of an SCR system in which an SCR sensor of the present invention is used.

As shown in FIG. 1, an SCR system 100 using an SCR sensor of the present invention mainly includes an SCR device 103 provided at an exhaust pipe 102 of an engine E, a dosing valve (urea injection device, dosing module) 104 for injecting urea aqueous solution on an upstream side of the SCR device 103 (upstream side of exhaust gas), a urea tank 105 for storing urea aqueous solution, a supply module 106 for supplying the urea aqueous solution stored in the urea tank 105 to the dosing valve 104, and a DCU (Dosing Control Unit) 126 for controlling the dosing valve 104, the supply module 106, and the like.

At the exhaust pipe 102 of the engine E, a DOC (Diesel Oxidation Catalyst) 107, a DPF (Diesel Particulate Filter) 108, and the SCR device 103 are sequentially arranged from the upstream side to the downstream side of exhaust gas. The DOC 107 generates $NO_2$ by oxidating NO in exhaust gas exhausted from the engine E, and increases a denitrification efficiency in the SCR device 103 by controlling a ratio of NO to $NO_2$ in the exhaust gas. Also, the DPF 108 traps a PM (Particulate Matter) in the exhaust gas.

The dosing valve 104 is provided at the exhaust pipe 102 on the upstream side of the SCR device 103. The dosing valve 104 is configured such that an injection nozzle is provided at a cylinder filled with high-pressure urea aqueous solution, and a valve body plugging the injection nozzle is attached to a plunger. By pulling up the plunger by electrifying a coil, the valve body is separated from the injection nozzle, so that the urea aqueous solution is injected. When electrifying the coil is stopped, the plunger is pulled down by an internal spring force and thus the valve body plugs the injection nozzle, so that the injection of the urea aqueous solution is stopped.

An exhaust gas temperature sensor 109 for measuring a temperature of the exhaust gas in an inlet of the SCR device 103 (SCR inlet temperature) is provided at the exhaust pipe 102 on an upstream side of the dosing valve 104. Also, an upstream NOx sensor 110 for detecting an NOx concentration in the upstream side of the SCR device 103 is provided on the upstream side of the SCR device 103 (herein, an upstream side of the exhaust gas temperature sensor 109), and a downstream NOx sensor 111 for detecting an NOx concentration in the downstream side of the SCR device 103 is provided on the downstream side of the SCR device 103.

The supply module 106 includes an SM pump 112 for pumping the urea aqueous solution, an SM temperature sensor 113 for measuring a temperature of the supply module 106 (temperature of the urea aqueous solution flowing through the supply module 106), a urea aqueous solution pressure sensor 114 for measuring a pressure of the urea aqueous solution in the supply module 106 (pressure in a discharge side of the SM pump 112), and a reverting valve 115 for switching a flow passage of the urea aqueous solution to supply the urea aqueous solution from the urea tank 105 to the dosing valve 104 or return the urea aqueous solution inside the dosing valve 104 to the urea tank 105. Herein, when the reverting valve 115 is turned on, the urea aqueous solution from the urea tank 105 is supplied to the dosing valve 104; and when the reverting valve 115 is turned off, the urea aqueous solution inside the dosing valve 104 is returned to the urea tank 105.

When the reverting valve 115 is switched to supply the urea aqueous solution to the dosing valve 104, the supply module 106 suctions the urea aqueous solution inside the urea tank 105 by the SM pump 112 through a liquid feed line (suction line) 116, supplies the urea aqueous solution to the dosing valve 104 through a pump line (pressure line) 117, and returns surplus urea aqueous solution to the urea tank 105 through a recovery line (back line) 118.

As described previously, the urea tank 105 is provided with an SCR sensor 119. The SCR sensor 119 includes a level sensor 120 for measuring a liquid surface height (level) of the urea aqueous solution inside the urea tank 105, a temperature sensor 121 for measuring a temperature of the urea aqueous solution inside the urea tank 105, and a quality sensor 122 for measuring a quality of the urea aqueous solution inside the urea tank 105. The quality sensor 122 detects the quality of the urea aqueous solution inside the urea tank 105 by detecting the concentration of the urea aqueous solution or detecting whether or not a heterogeneous mixture is mixed in the urea aqueous solution, for example, from a propagation speed of an ultrasonic wave or an electrical conductivity.

A cooling line 123 for circulating cooling aqueous solution for cooling the engine E is connected to the urea tank 105 and the supply module 106. The cooling line 123 performs heat exchange between the cooling aqueous solution flowing through the urea tank 105 into the cooling line 123 and the urea aqueous solution inside the urea tank 105. Likewise, the cooling line 123 performs heat exchange between the cooling aqueous solution flowing through the supply module 106 into the cooling line 123 and the urea aqueous solution inside the supply module 106.

The cooling line 123 is provided with a tank heater valve (coolant valve) 124 for switching whether or not to supply the cooling aqueous solution to the urea tank 105 and the supply module 106. In addition, although the cooling line 123 is also connected to the dosing valve 104, the cooling aqueous solution is supplied to the dosing valve 104 regardless of the on/off of the tank heater valve 124. In addition, although not shown in FIG. 1 for simplicity, the cooling line 123 is disposed along the liquid feed line 116, the pump line 117, and the recovery line 118 through which the urea aqueous solution flows.

Figure 2:
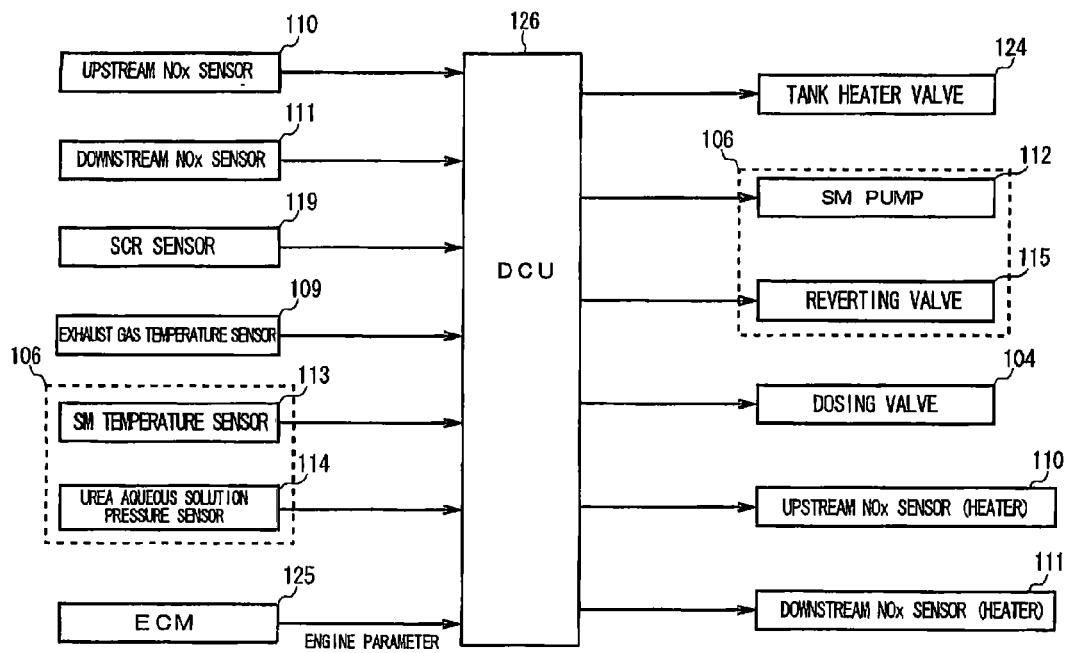
FIG. 2 is an input/output configuration diagram of the SCR system of FIG. 1.

FIG. 2 shows an input/output configuration diagram of the DCU 126.

As shown in FIG. 2, an input signal line from an ECM (Engine Control Module) 125 controlling the upstream NOx sensor 110, the downstream NOx sensor 111, the SCR sensor 119 (level sensor 120, temperature sensor 121, quality sensor 122), the exhaust gas temperature sensor 109, the SM temperature sensor 113 and the urea aqueous solution pressure sensor 114 of the supply module 106, and the engine E is connected to the DCU 126. Signals of engine parameters (the number of rotations of the engine, and the like) are input from the ECM 125.

Also, output signal lines to the tank heater valve 124, the SM pump 112 and the reverting valve 115 of the supply module 106, the dosing valve 104, a heater of the upstream NOx sensor 110, a heater of the downstream NOx sensor 111, and a remaining amount indicator 2 are connected to the DCU 126. Also, the input/output of signals between the DCU 126 and the respective members may be any one of the input/output through separate signal lines and the input/output through a CAN (Controller Area Network).

The DCU 126 estimates an amount of NOx in the exhaust gas based on the engine parameter signals from the ECM 125 and the temperature of the exhaust gas from the exhaust gas temperature sensor 109, and determines an amount of urea aqueous solution to be injected from the dosing valve 104 based on the estimated amount of NOx in the exhaust gas. In addition, when the determined amount of urea aqueous solution is injected by the dosing valve 104, the DCU 126 controls the dosing valve 104 based on the detection value of the upstream NOx sensor 110 to adjust the amount of urea aqueous solution to be injected from the dosing valve 104.

Figure 3:
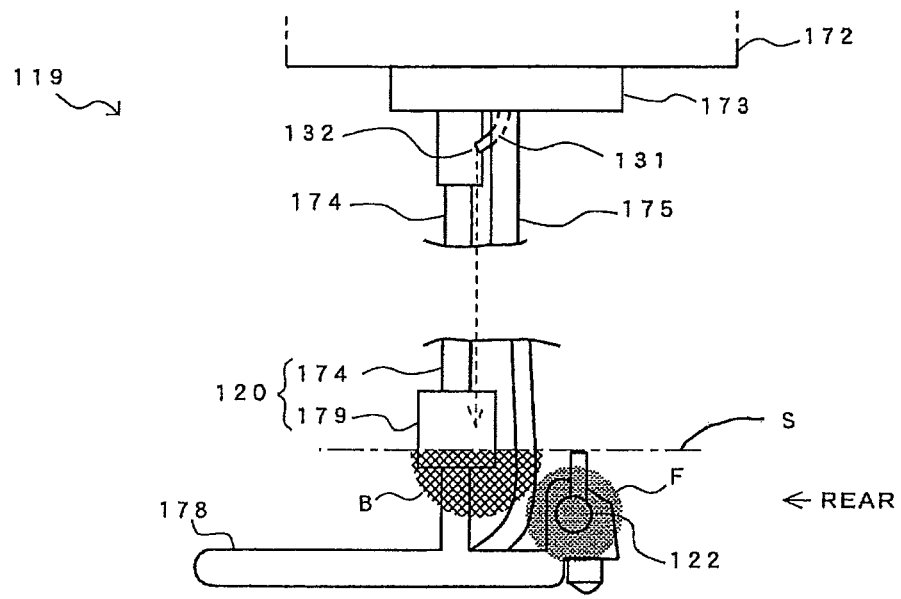
FIG. 3 is an enlarged side view of part of the SCR sensor of the present invention.

As shown in FIG. 3, in the SCR sensor 119 according to the present invention, the quality sensor 122 measuring a quality of the urea aqueous solution inside the urea tank 105 is installed between the minimum remaining amount liquid level S and the bottom portion 105b (see FIG. 7) of the urea tank 105. A drop pipe 131 drops the urea aqueous solution, which is dispensed from the urea tank 105 and temporarily stored outside the urea tank 105 and then recovered, into the urea tank 105. The drop pipe 131 is installed from the ceiling portion 105a (see FIG. 7) of the urea tank 105 to a top space of the urea tank 105. In the SCR sensor 119, as the level sensor 120, the support 174 guiding the float 179 for liquid level detection is installed from the bottom portion to the ceiling portion of the urea tank 105. As in the SCR sensor 171 described with reference to FIG. 7, in the SCR sensor 119, the quality sensor 122 and the drop pipe 131 are integrated through the support 174, and the dispensing pipe 175 for dispensing the urea aqueous solution from the urea tank 105 is installed along the support 174.

Figure 4:
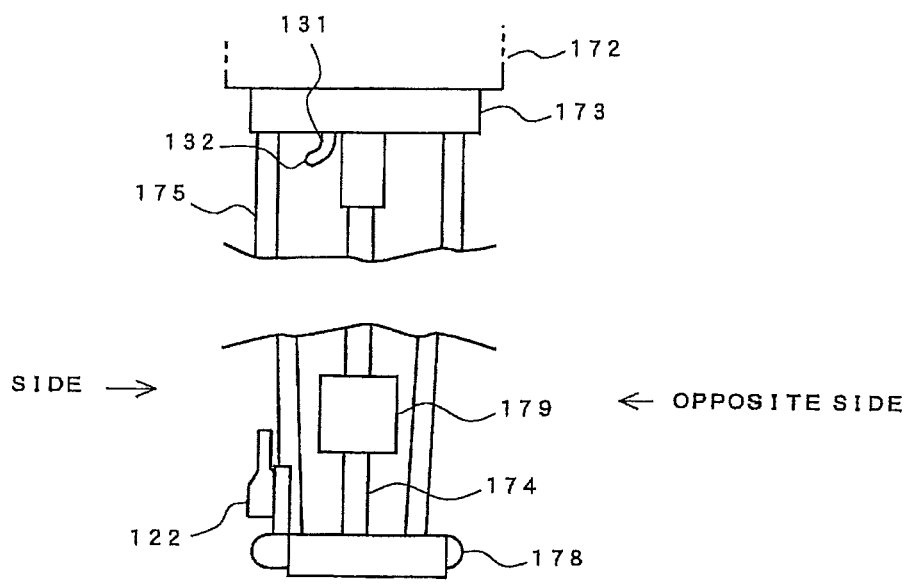
FIG. 4 is an enlarged rear view of part of the SCR sensor of the present invention.
Figure 8:
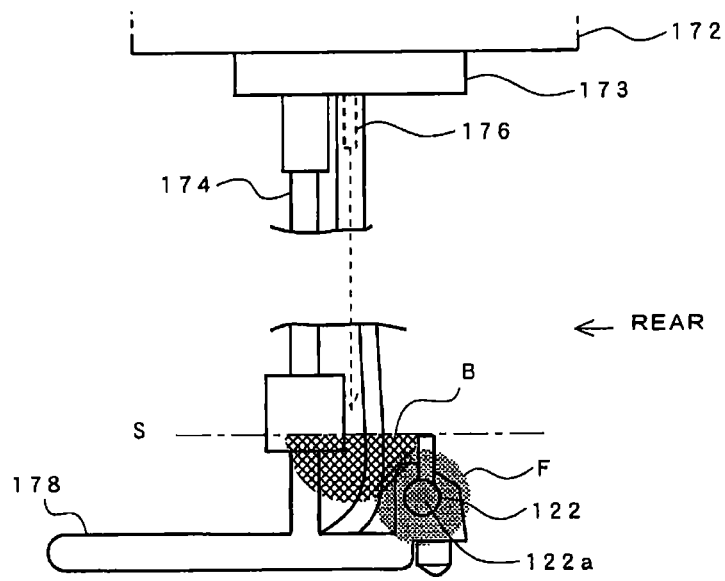
FIG. 8 is an enlarged side view of part of an SCR sensor.
Figure 9:
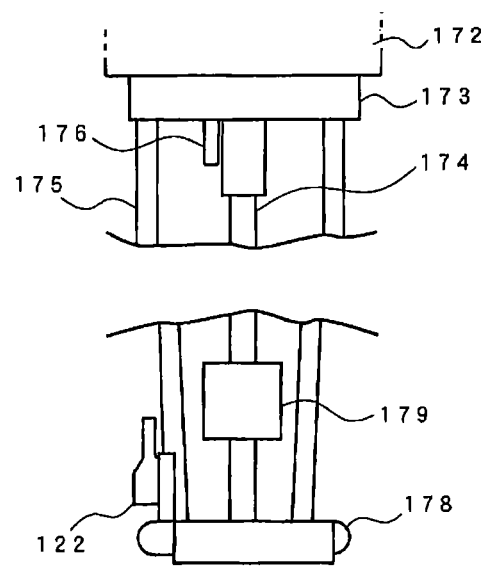
FIG. 9 is an enlarged rear view of part of an SCR sensor.
Figure 10:
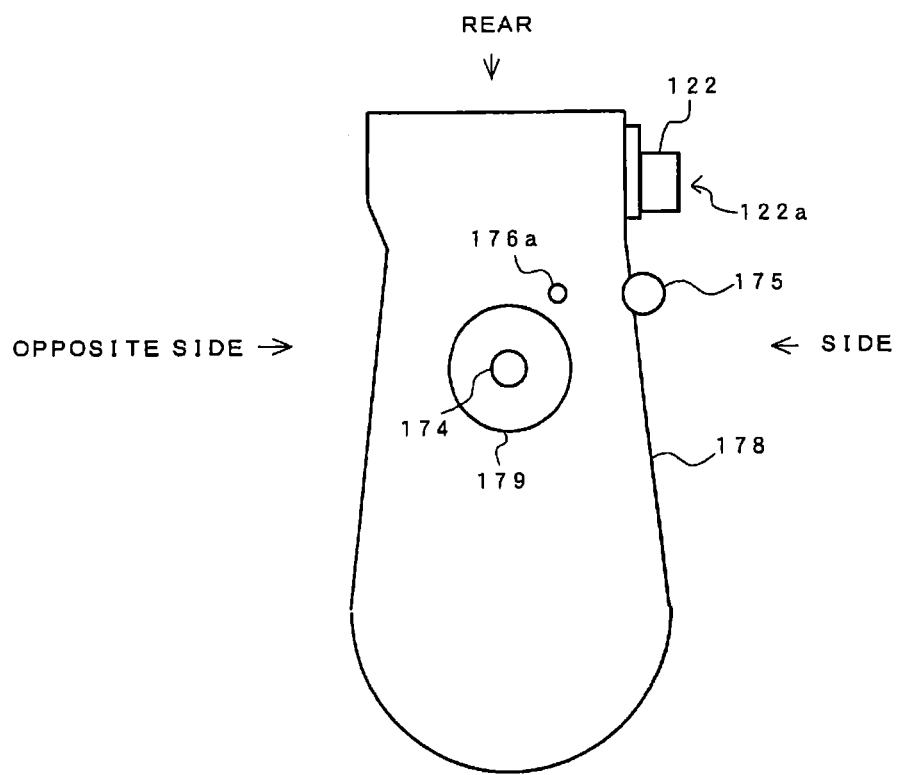
FIG. 10 is a top arrangement view of an SCR sensor.

The prominent feature of the SCR sensor 119 according to the present invention is that the bubble diffusion region B by the urea aqueous solution dropping from the drop pipe 131 is out of the sensitive region F of the quality sensor 122. Specifically, as shown in the side view of FIG. 3, the drop pipe 131 is inserted into the top pedestal 173 at the same position as the drop pipe 176 of the SCR sensor 119 shown in FIG. 8, but is bent toward the support 174 at a lower portion in the urea tank 105. Also, as shown in the rear view of FIG. 4, the drop pipe 131 is inserted into the top pedestal 173 at the same position as the drop pipe 176 of the SCR sensor 119 shown in FIG. 9, but is bent toward the dispensing pipe 175 at a lower portion in the urea tank 105.

Figure 5:
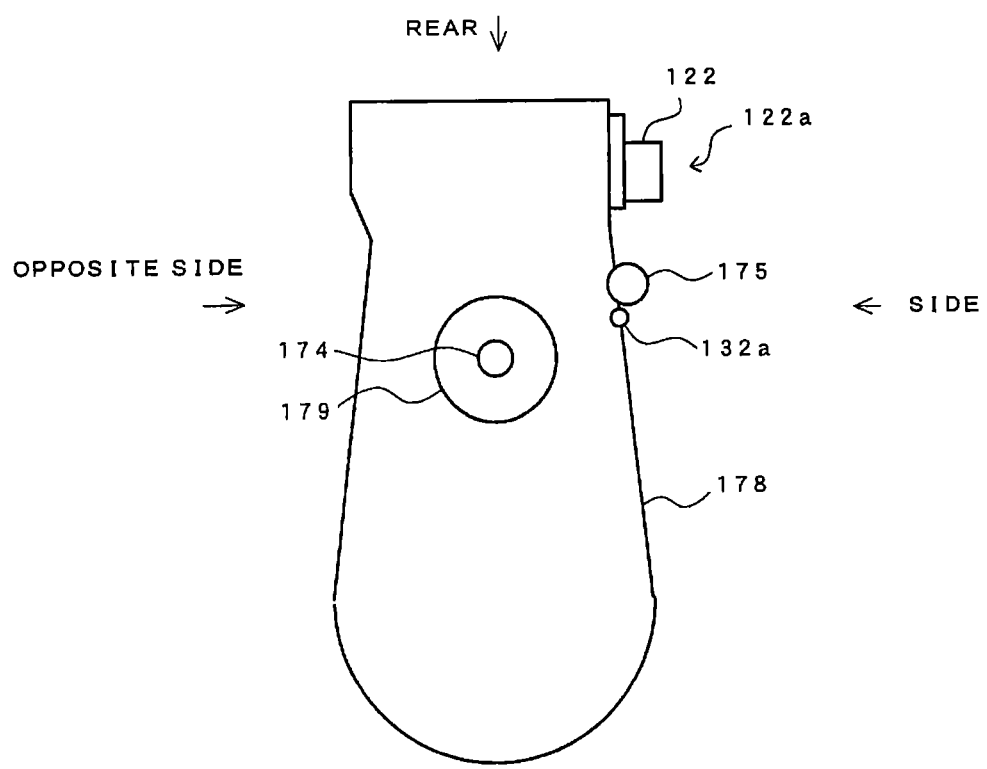
FIG. 5 is a top arrangement view of the SCR sensor of the present invention.

As shown in FIG. 5, a virtual drop opening 132a is shown in a top arrangement view by projecting a drop opening 132 of the drop pipe 131. While the quality sensor 122 is located at one side of the dispensing pipe 175, the virtual drop opening 132a is located at an opposite side with respect to the quality sensor 122 of the dispensing pipe 175. Therefore, it can be seen that the quality sensor 122 is disposed at one side of the dispensing pipe 175, and the drop opening 132 of the drop pipe 131 is disposed at an opposite side with respect to the quality sensor 122 of the dispensing pipe 175.

By the above configuration, the SCR sensor 119 according to the present invention exhibits operational effects such as the following.

As shown in FIG. 3, when the urea aqueous solution in the urea tank 105 is reduced to near the minimum remaining amount liquid level S, bubbles caused by the urea aqueous solution dropped from the drop pipe 176 are diffused into the bubble diffusion region B. However, the bubble diffusion region B by the urea aqueous solution dropping from the drop pipe 131 is out of the sensitive region F of the quality sensor 122, and the bubbles are not diffused into the sensitive region F of the quality sensor 122. Therefore, the quality sensor 122 normally functions, and the measurement accuracy thereof does not degrade.

Also, since the drop opening 132 of the drop pipe 131 is disposed at the opposite side with respect to the quality sensor 122 of the dispensing pipe 175, the urea aqueous solution dropped from the drop opening 132 reaches the liquid level of the urea aqueous solution at the position of the virtual drop opening 132a, as shown in FIG. 5. In this manner, since the position of the dropped urea aqueous solution reaching the liquid level is opposite to the quality sensor 122 with the dispensing pipe 175 interposed therebetween, bubbles generated under the liquid level are blocked by the dispensing pipe 175, so that the diffusion of the bubbles toward the quality sensor 122 is difficult. Therefore, the bubbles are not diffused into the sensitive region F of the quality sensor 122.

As described above, according to the SCR sensor 119 of the present invention, since the bubble diffusion region B caused by the urea aqueous solution dropping from the drop pipe 131 is out of the sensitive region F of the quality sensor 122, the bubbles are not diffused into the sensitive region F of the quality sensor 122. Therefore, even when the remaining amount of the urea tank 105 is reduced, the quality sensor 122 normally functions and the measurement accuracy thereof does not degrade.

Also, in this embodiment, the drop pipe 131 is disposed at the same top side position as the drop pipe 176 of the SCR sensor 119 with respect to the top pedestal 173, and the drop pipe 131 is bent such that the drop opening 132 is located at a position deviated from the position. However, the present invention is not limited thereto, and the bubble diffusion region B may be out of the sensitive region F of the quality sensor 122 by changing the top side position of the drop pipe 131 with respect to the top pedestal 173.

The invention claimed is:

1. An SCR sensor, comprising:
   a quality sensor for measuring a liquid quality between a minimum remaining amount liquid level and a bottom portion of a liquid tank;
   a drop pipe having a drop opening at an upper portion of the liquid tank above the liquid level,
   wherein the sensor and the drop pipe are connected to a support and together form an assembly extending downward from the upper portion of the liquid tank into the liquid tank,
   wherein the support guides a float for detecting the liquid level of the tank,
   wherein a dispensing pipe for dispensing liquid from the liquid tank is installed along the support,
   wherein the quality sensor is disposed at one side of the dispensing pipe, and
   wherein the drop opening is disposed on an opposite side of the quality sensor with the dispensing pipe interposed therebetween; and
   a bubble diffusion region caused by liquid dropping from the drop pipe and being spaced from a sensitive region of the quality sensor.

2. The SCR sensor according to claim 1, wherein the drop pipe is bent relative to a longitudinal axis of the support.

3. An SCR sensor attached to a urea tank storing urea aqueous solution for purifying exhaust gas of an engine, comprising:
   a quality sensor for measuring a quality of the urea aqueous solution inside the urea tank and being installed between a minimum remaining amount liquid level and a bottom portion of the urea tank;
   a drop pipe for dropping the urea aqueous solution, which solution is dispensed from the urea tank and temporarily stored outside the urea tank and then recovered, into the urea tank is installed in an upper portion of the urea tank above the liquid level;
   a support guiding a float for detecting a level of the urea aqueous solution in the tank and being installed from the bottom portion to the ceiling portion of the urea tank,
   wherein the quality sensor and the drop pipe are connected to the support,
   wherein a dispensing pipe for dispensinq the urea aqueous solution from the liquid tank is installed along the support,
   wherein the quality sensor is disposed at one side of the dispensing pipe, and
   wherein the drop opening is disposed on an opposite side of the quality sensor with the dispensing pipe interposed therebetween; and
   a bubble diffusion region caused by the urea aqueous solution dropping from the drop pipe and being spaced from a sensitive region of the quality sensor.

4. The SCR sensor according to claim 3, wherein
   an assembly is formed by connecting the quality sensor, the drop pipe and the support, and the assembly extends through an attachment hole formed at the upper portion of the urea tank and into the tank.

5. The SCR sensor according to claim 3, wherein the drop pipe is bent relative to a longitudinal axis of the support.

* * * * *